(12) United States Patent
Sawada et al.

(10) Patent No.: US 11,786,223 B2
(45) Date of Patent: Oct. 17, 2023

(54) ULTRASONIC PROBE WITH HEAT DISSIPATION MEMBERS ARRANGED IN CENTER OF BACKING LAYER

(71) Applicant: Hitachi, Ltd., Tokyo (JP)

(72) Inventors: Wataru Sawada, Tokyo (JP); Toru Watanabe, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 207 days.

(21) Appl. No.: 17/189,292

(22) Filed: Mar. 2, 2021

(65) Prior Publication Data

US 2021/0353263 A1 Nov. 18, 2021

(30) Foreign Application Priority Data

May 14, 2020 (JP) .................................. 2020-085104

(51) Int. Cl.
*A61B 8/00* (2006.01)
*B06B 1/06* (2006.01)
(Continued)

(52) U.S. Cl.
CPC ............ *A61B 8/546* (2013.01); *A61B 8/4488* (2013.01); *B06B 1/067* (2013.01); *B06B 1/0622* (2013.01);
(Continued)

(58) Field of Classification Search
CPC ..... A61B 8/546; A61B 8/4488; A61B 8/4494; A61B 8/4444; B06B 1/0622; B06B 1/067;
(Continued)

(56) References Cited

U.S. PATENT DOCUMENTS

2005/0075573 A1* 8/2005 Park .................. A61B 8/546
600/459
2007/0276248 A1* 11/2007 Saito .................. A61B 8/546
600/459
(Continued)

FOREIGN PATENT DOCUMENTS

JP 2005-103078 A 4/2005
JP 2013-115537 A 6/2013

OTHER PUBLICATIONS

Chinese Office Action received in corresponding Chinese Application No. 202110238008.1 dated Jun. 29, 2023.

*Primary Examiner* — Christopher Koharski
*Assistant Examiner* — Gabriel Victor Popescu
(74) *Attorney, Agent, or Firm* — MATTINGLY & MALUR, PC

(57) ABSTRACT

An ultrasonic probe has a transduction layer in which a plurality of transducers are placed, a backing layer provided at a rear side of the transduction layer with a wiring layer therebetween, and a plurality of heat dissipation members provided in the backing layer. The plurality of heat dissipation members extend in a line form in the backing layer, and are placed with an aligned direction of extension. An area occupancy percentage of the heat dissipation member at a center region of the backing layer is larger than that at an outer side of the center region. The center region is not positioned at ends of the cross section intersecting the direction of extension of the heat dissipation member, includes a center of gravity of the cross section, and occupies an area less than or equal to a half of an area of the cross section.

10 Claims, 9 Drawing Sheets

(51) Int. Cl.
*H10N 30/80* (2023.01)
*H10N 30/87* (2023.01)

(52) U.S. Cl.
CPC .......... *H10N 30/80* (2023.02); *H10N 30/875* (2023.02); *B06B 2201/76* (2013.01)

(58) Field of Classification Search
CPC . B06B 2201/76; B06B 1/0629; B06B 1/0677; H01L 41/04; H01L 41/0475; H01L 41/1132; H01L 41/1875; H01L 41/0474; H01L 41/1876; G01S 7/52079
See application file for complete search history.

(56) References Cited

U.S. PATENT DOCUMENTS

| | | | |
|---|---|---|---|
| 2011/0074458 A1* | 3/2011 | Di Stefano | G01R 31/2863 324/757.01 |
| 2013/0134834 A1 | 5/2013 | Yoshikawa et al. | |
| 2019/0209140 A1* | 7/2019 | Jung | G01N 29/228 |

* cited by examiner ional signals supplied to the transducers, and the ultrasonic beam is electrically scanned. Further, the electrical signals which are output from the transducers are phase-aligned and summed, and a reception signal is produced which is based on the ultrasound arriving from a direction of the ultrasonic beam.

ULTRASONIC PROBE WITH HEAT DISSIPATION MEMBERS ARRANGED IN CENTER OF BACKING LAYER

CROSS REFERENCE TO RELATED APPLICATION

This application claims priority to Japanese Patent Application No. 2020-085104 filed on May 14, 2020, which is incorporated herein by reference in its entirety including the specification, claims, drawings, and abstract.

TECHNICAL FIELD

The present disclosure relates to an ultrasonic probe, and in particular to a structure for discharging heat generated by a transducer.

BACKGROUND

Ultrasound diagnostic apparatuses are in wide use. In an ultrasound diagnostic apparatus, ultrasound is transmitted to a subject, ultrasound reflected from inside the subject is received, and data of an image indicating a tissue within the subject are produced based on the received ultrasound. The ultrasound diagnostic apparatus comprises an ultrasonic probe which transmits ultrasound according to a supplied electrical signal, and which outputs an electrical signal according to received ultrasound. In general, a plurality of transducers are arranged in the ultrasonic probe. An ultrasonic beam is formed by adjusting delay times of the electrical signals supplied to the transducers, and the ultrasonic beam is electrically scanned. Further, the electrical signals which are output from the transducers are phase-aligned and summed, and a reception signal is produced which is based on the ultrasound arriving from a direction of the ultrasonic beam.

When the ultrasonic probe transmits the ultrasound, heat is generated in the transducer. Because of this, as described in JP 2013-115537 A, a transmission power may be limited so that the temperature of the transducer does not become too high, in which case, the capability of the ultrasonic probe may fail to be fully utilized. Thus, in the ultrasonic probe, a structure is employed to discharge, from the ultrasonic probe, the heat generated by the transducer, as described in JP 2005-103078 A and JP 2013-115537 A.

In general, a larger amount of heat is generated at a center part of the ultrasonic probe, from a region near a center of a surface which contacts the subject to an inside of the ultrasonic probe, than in a region outside of the center part. Because of this, in the ultrasonic probe of the related art, heat dissipation at the center part may in some cases be insufficient.

An advantage of the present disclosure lies in provision of a structure which enables sufficient heat dissipation of an ultrasonic probe having a plurality of transducers.

SUMMARY

According to one aspect of the present disclosure, there is provided an ultrasonic probe comprising: a transduction layer in which a plurality of transducers are placed; a backing layer provided at a rear side of the transduction layer; and a plurality of heat dissipation members which are provided in the backing layer, which extend in a line form in the backing layer, and which are placed with an aligned direction of extension, wherein an area occupancy percentage of the heat dissipation member at a center region of the backing layer in a cross section intersecting the direction of extension of the heat dissipation member is larger than that of a region at an outer side of the center region.

According to an aspect of the present disclosure, heat dissipation of the ultrasonic probe having a plurality of transducers can be sufficiently achieved.

BRIEF DESCRIPTION OF DRAWINGS

Embodiment(s) of the present disclosure will be described based on the following figures, wherein.

DESCRIPTION OF EMBODIMENTS

Figure 1:
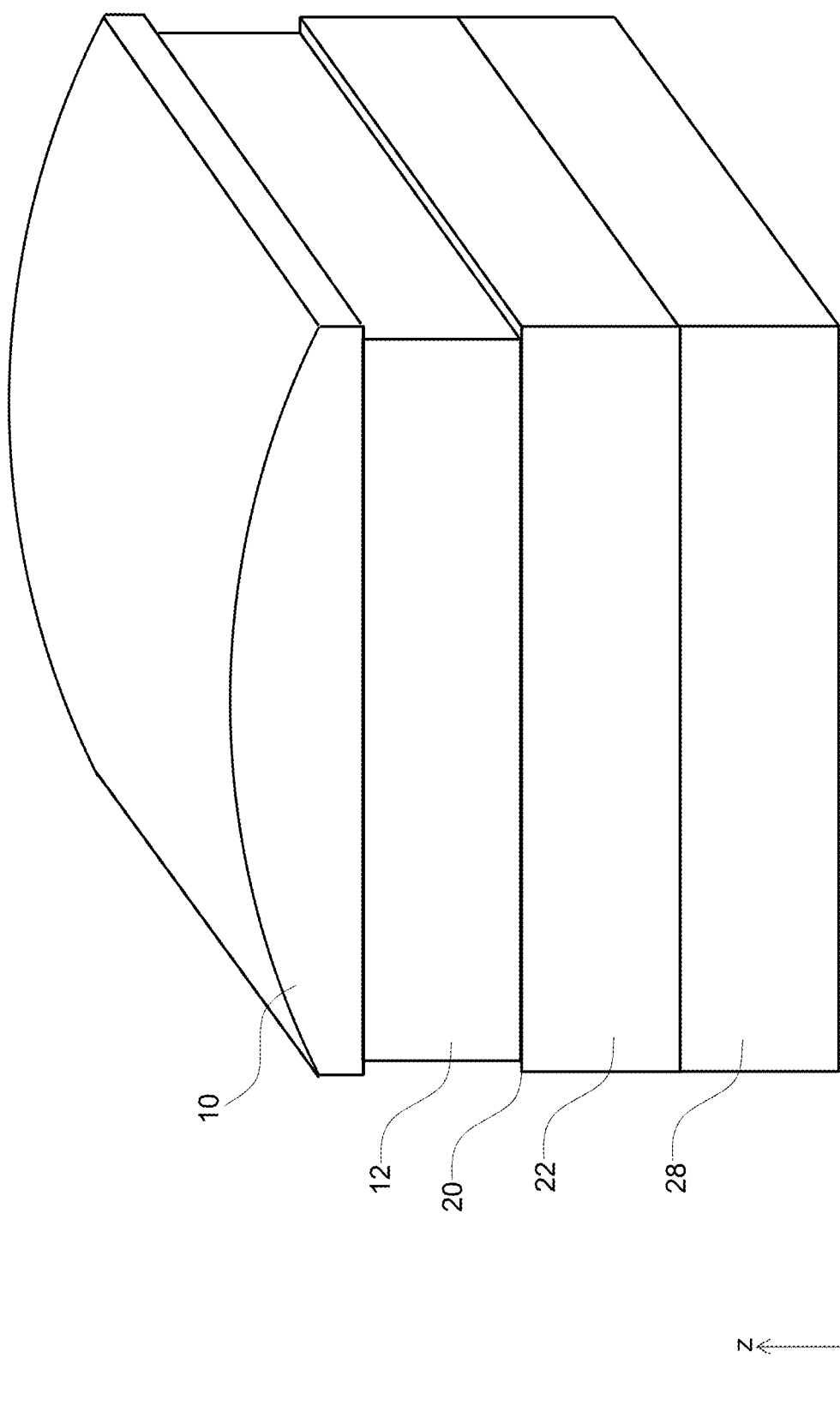
FIG. 1 is a perspective diagram of an ultrasonic probe.

Embodiments of the present disclosure will now be described with reference to the drawings. Identical constituent elements shown in a plurality of figures will be assigned the same reference numerals and will not be repeatedly described. In the present disclosure, a term "front" means a direction viewing a side of a subject from an ultrasonic probe, and a term "rear" means a direction viewing a side of the ultrasonic probe from the subject. In addition, in the present disclosure, the terms of "right" and "left" mean right and left in the figures. These terms indicating the directions are for the purposes of description only, and the orientation of the ultrasonic probe in use is not limited. In the figures, a front direction is set as a positive direction on a z axis, and an xy plane is defined which is perpendicular to the z axis.

FIG. 1 schematically shows a perspective diagram of an ultrasonic probe according to a first embodiment of the present disclosure. The ultrasonic probe comprises a protective layer 10, a transduction layer 12, a wiring layer 20, a backing layer 22, and a heat dissipation layer 28. The protective layer 10, the transduction layer 12, the wiring layer 20, the backing layer 22, and the heat dissipation layer 28 are layered in this order in a front-and-rear direction. Ratios of thicknesses of the layers shown in FIG. 1 are changed for ease of description, and differ from the ratios of the actual thicknesses. This is similarly applicable to the ratios of the thicknesses of the layers shown in other figures. The protective layer 10 covers a front side of the transduction layer 12, and mechanically protects the transduction layer 12. The protective layer 10 has a front surface contacting a subject, propagates to the subject ultrasound emitted from the transduction layer 12, and propagates to the transduction layer 12 ultrasound reflected by the subject.

The front surface of the protective layer 10 is a two-dimensionally curved surface. That is, the front surface of the protective layer 10 forms a convex-up curve in a cross section in a direction of a long axis (plane parallel to a yz plane) which is a cross section perpendicular to a direction of a short axis (x axis direction), and forms a straight line in a cross section in the direction of the short axis (plane parallel to a zx plane) which is a cross section perpendicular to the direction of the long axis (y axis direction). The protective layer 10 may be formed from silicone rubber or the like. The long axis direction is defined as a longitudinal direction of the transducer to be described later, and the short axis direction is defined as a direction perpendicular to the long axis direction and to the front-and-rear direction.

The transduction layer 12 has a plurality of transducers, as will be described later. The wiring layer 20 is formed from a layer-form member formed from an insulating material, and a conductor line for electrical wiring, placed over the layer-form member. The wiring layer 20 may be an FPC (Flexible Printed Circuit). The wiring layer 20 connects each of the plurality of transducers formed in the transduction layer 12 to transmission and reception circuits of an ultrasound diagnosis apparatus. Each of the transducers in the transduction layer 12 generates ultrasound in response to an electrical signal which is supplied from the wiring layer 20, and outputs an electrical signal to the wiring layer 20 based on the received ultrasound.

The backing layer 22 attenuates ultrasound emitted from the transduction layer 12 toward the rear side. The heat dissipation layer 28 discharges heat generated in the ultrasonic probe to the rear side. The heat dissipation layer 28 may be formed from a metal material including aluminum, copper, or the like.

Figure 2:
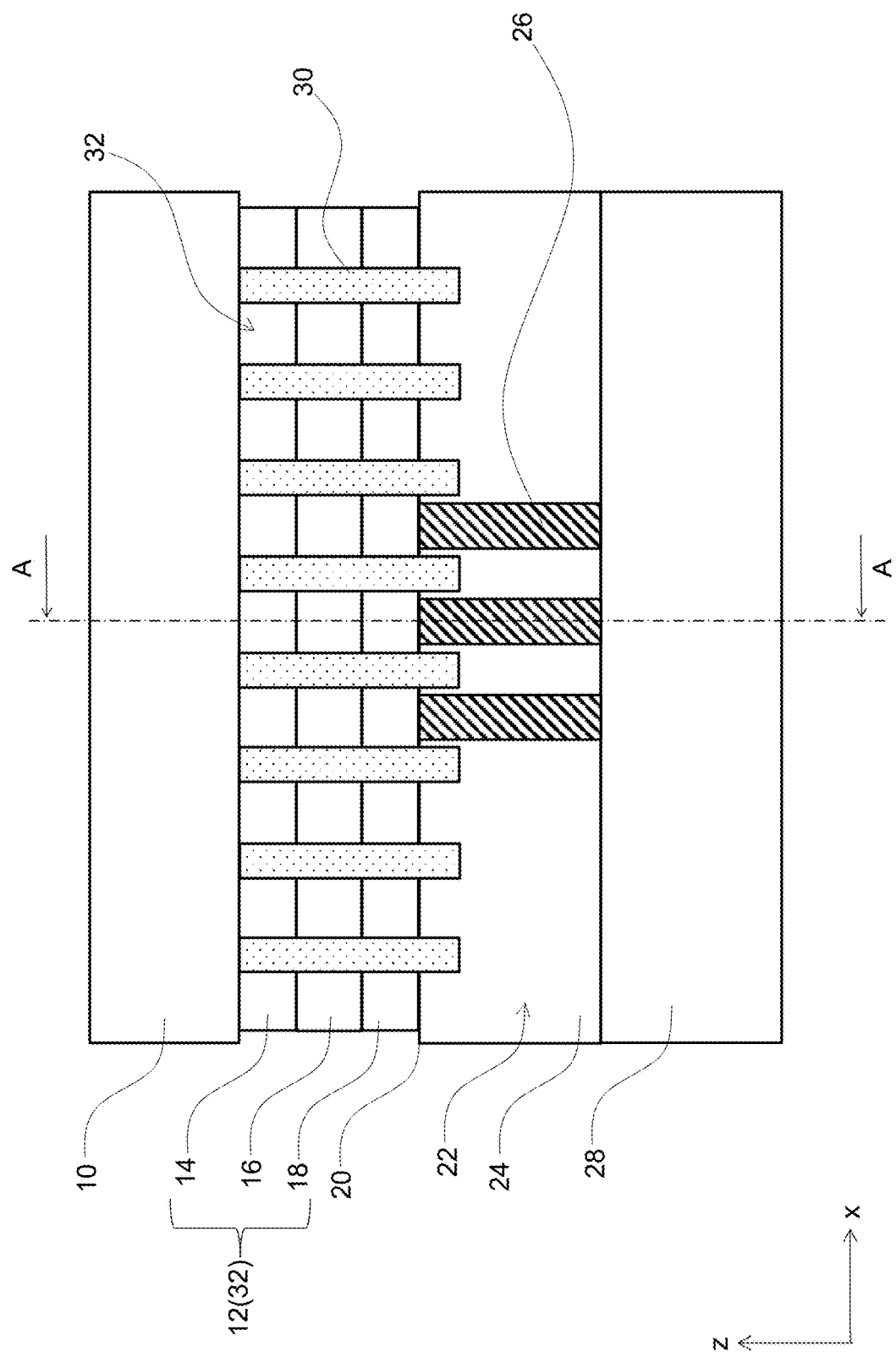
FIG. 2 is a schematic diagram showing a cross section in a short axis direction of an ultrasonic probe.
Figure 3:
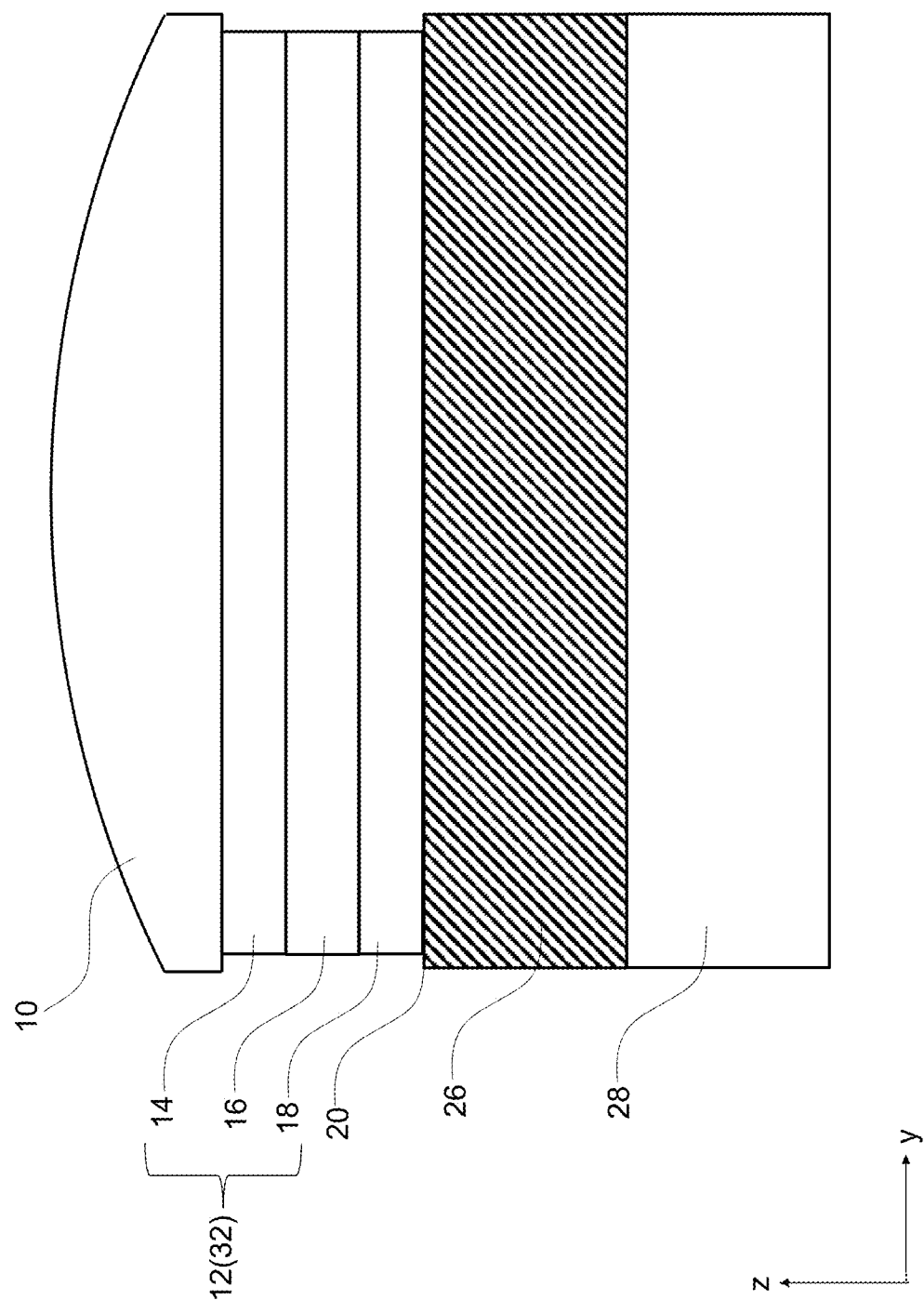
FIG. 3 is a schematic diagram showing a cross section in a long axis direction of an ultrasonic probe.

FIG. 2 schematically shows a cross section of the ultrasonic probe in the short axis direction. FIG. 3 shows a cross section in the long axis direction when the ultrasonic probe is cut along a line AA in FIG. 2. The transduction layer 12 comprises an acoustic matching layer 14, a transducer layer 16, and a hard backing layer 18. The acoustic matching layer 14, the transducer layer 16, and the hard backing layer 18 are layered in this order in the front-and-rear direction. The transduction layer 12 is divided by a plurality of cut grooves 30 which are parallel to the cross section in the long axis direction, and each of the portions divided by the plurality of cut grooves 30 forms a transducer 32.

The cut groove 30 extends from the front surface of the transduction layer 12 to a rear surface, and to the wiring layer 20 and the backing layer 22 at the rear side. Each transducer 32 has a quadrangular pillar shape extending in the long axis direction. In the example configuration of FIG. 2, a length of each transducer 32 in the front-and-rear direction is longer than a length in the short axis direction, and each transducer 32 is formed in a plate shape. In the example configuration of FIG. 2, eight cut grooves 30 are formed in equal intervals in the short axis direction, and nine transducers 32 are thereby formed. FIG. 2 schematically shows an ultrasonic probe including nine transducers 32, but the transduction layer 12 may include the transducers 32 in a number of 100 or more and 300 or less.

The transducer layer 16 may be formed from a piezoelectric material such as PZT (lead zirconate titanate), PMN-PT, or the like. In each transducer 32, the acoustic matching layer 14 improves a transmission efficiency of ultrasound transmitted from the transducer layer 16 to the subject, by a matching action with respect to an acoustic impedance. In addition, in each transducer 32, the acoustic matching layer 14 improves a transmission efficiency of ultrasound reflected by the subject and transmitted through the protective layer 10 to the transducer layer 16, by a matching action with respect to the acoustic impedance.

The hard backing layer 18 reflects the ultrasound emitted from the transducer layer 16 to the rear side. The hard backing layer 18 may be formed from a metal material including tungsten carbide or the like.

In the backing layer 22, a plurality of heat dissipation members 26 are provided in a backing material 24. The backing material 24 may be formed by mixing an attenuation filler in a powder form in a resin. For the attenuation filler, for example, a metal, ceramics, or the like may be employed.

The heat dissipation member 26 has a quadrangular pillar shape extending in the long axis direction. In the example configuration of FIG. 2, a length of each heat dissipation member 26 in the front-and-rear direction is longer than a length in the short axis direction, and each heat dissipation member 26 is formed in a plate shape. Each heat dissipation member 26 is provided at a position between cut grooves 30 between adjacent transducer elements 32. FIG. 2 schematically shows an example configuration in which three heat dissipation members 26 are provided. The heat dissipation member 26 may be formed by a ceramic material having sufficient rigidity and sufficient heat conductivity, such as aluminum oxide, silicon nitride, aluminum nitride, or the like.

Figure 4:
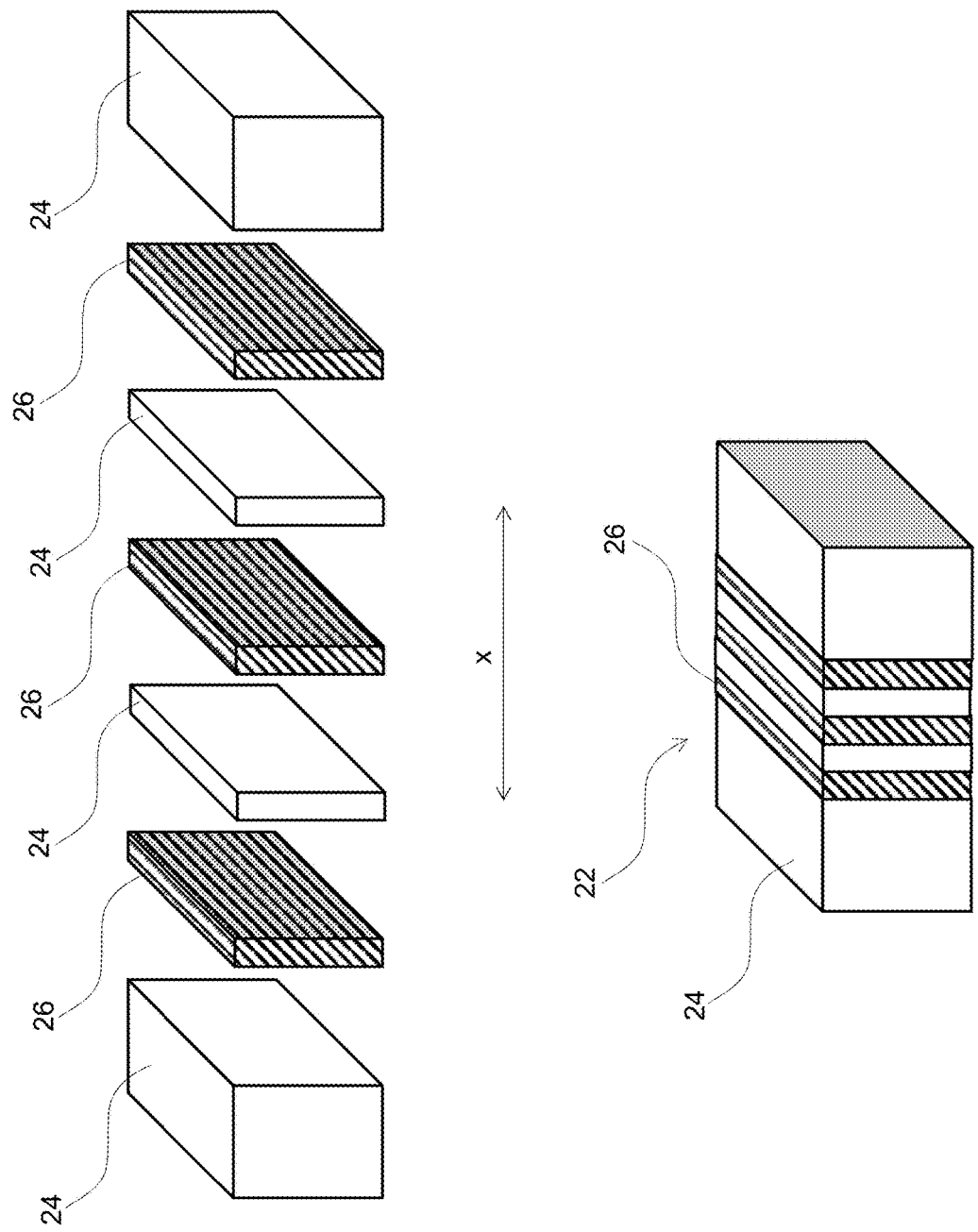
FIG. 4 is a diagram showing a manufacturing process of a backing layer.

FIG. 4 shows a manufacturing process of the backing layer 22. As shown at an upper side of FIG. 4, the heat dissipation member 26 is sandwiched between the backing materials 24 having a quadrangular pillar shape. The backing materials 24 and the heat dissipation members 26 are alternately placed and joined. With this process, as shown at a lower side of FIG. 4, the backing material 24 and the heat dissipation member 26 are integrated.

The transduction layer 12 and the backing layer 22 may be manufactured in the following process. Namely, after the acoustic matching layer 14, the transducer layer 16, the hard backing layer 18, the wiring layer 20, and the backing layer 22 are layered, the plurality of cut grooves 30 are formed extending from the front surface of the acoustic matching layer 14 toward the rear side, to the backing layer 22.

As described, the ultrasonic probe of the present embodiment has the transduction layer 12 in which the plurality of transducers 32 are placed, the backing layer 22 provided at the rear side of the transduction layer 12 with the wiring layer 20 therebetween, and the plurality of heat dissipation members 26 provided in the backing layer 22. The plurality of heat dissipation members 26 extend in a line form in the backing layer 22, and are placed with an aligned direction of extension. An area occupancy percentage of the heat dissipation member 26 at a center region of the backing layer 22 (center region in a cross section intersecting the direction of the heat dissipation member 26) is larger than an area occupancy percentage of the heat dissipation member 26 at an outer side of the center region.

Here, the center region is a region which is not positioned at ends of the cross section in the short axis direction, which includes a center of gravity of the cross section in the short axis direction, and which occupies an area which is less than or equal to half of an area of the cross section in the short axis direction. An area of each region at the ends of the cross section in the short axis direction, which is not the center region, is set, for example, to be greater than or equal to ⅛ of the area of the cross section in the short axis direction. Thus, in the ultrasonic probe of the present embodiment, a volume occupancy percentage of the heat dissipation member 26 at a three-dimensional center region extending in the long axis direction with the center region of the cross section in the short axis direction as a cross section is larger than a volume occupancy percentage of the heat dissipation member 26 at an outer side of the three-dimensional center region.

In the example configuration of FIG. 2, the center region is a region occupying less than or equal to ⅓ of the cross section in the short axis direction, at the center of the cross section in the short axis direction. Specifically, the center region is a region surrounded by a left-side boundary line which extends in the front-and-rear direction at a right side by ⅓ from a vertical side on the left of the figure of the cross section in the short axis direction, and a right-side boundary line which extends in the front-and-rear direction at a left side by ⅓ from a vertical side on the right side of the figure of the cross section in the short axis direction. The center of gravity of the center region coincides with the center of gravity of the cross section in the short axis direction. No heat dissipation member is provided in a region at the outer side of the center region. The heat dissipation member 26 is in thermal contact with the transducer 32 through the wiring layer 20. The heat generated by the transducer 32 is transferred by the heat dissipation member 26 at the rear side of the transducer 32 to the heat dissipation layer 28.

In the ultrasonic probe of the present embodiment, the area occupancy percentage of the heat dissipation member 26 at the center region of the cross section in the short axis direction is larger than the area occupancy percentage of the heat dissipation member 26 at the outer side of the center region. With this configuration, a heat dissipation effect at the center part from a region near the center of the front surface of the protective layer 10 to the inside can be improved. In the ultrasonic probe, an amount of heat generation is greater at the center part. Thus, according to the present embodiment, the amount of temperature increase of the overall ultrasonic probe can be suppressed. Further, a volume of the heat dissipation member 26 included in the backing layer 22 can be reduced, resulting in an improved effect of attenuation of the ultrasound at the backing layer 22.

In addition, in the ultrasonic probe of the present embodiment, the heat dissipation member 26 is provided at a position between the cut grooves 30 between adjacent transducers 32. With this configuration, in the case where the cut groove 30 is formed after the acoustic matching layer 14, the transducer layer 16, the hard backing layer 18, the wiring layer 20, and the backing layer 22 are layered, contact of a tool for forming the cut groove 30 with the heat dissipation member 26 can be avoided, thereby preventing shortening of the lifetime of the tool.

Figure 5:
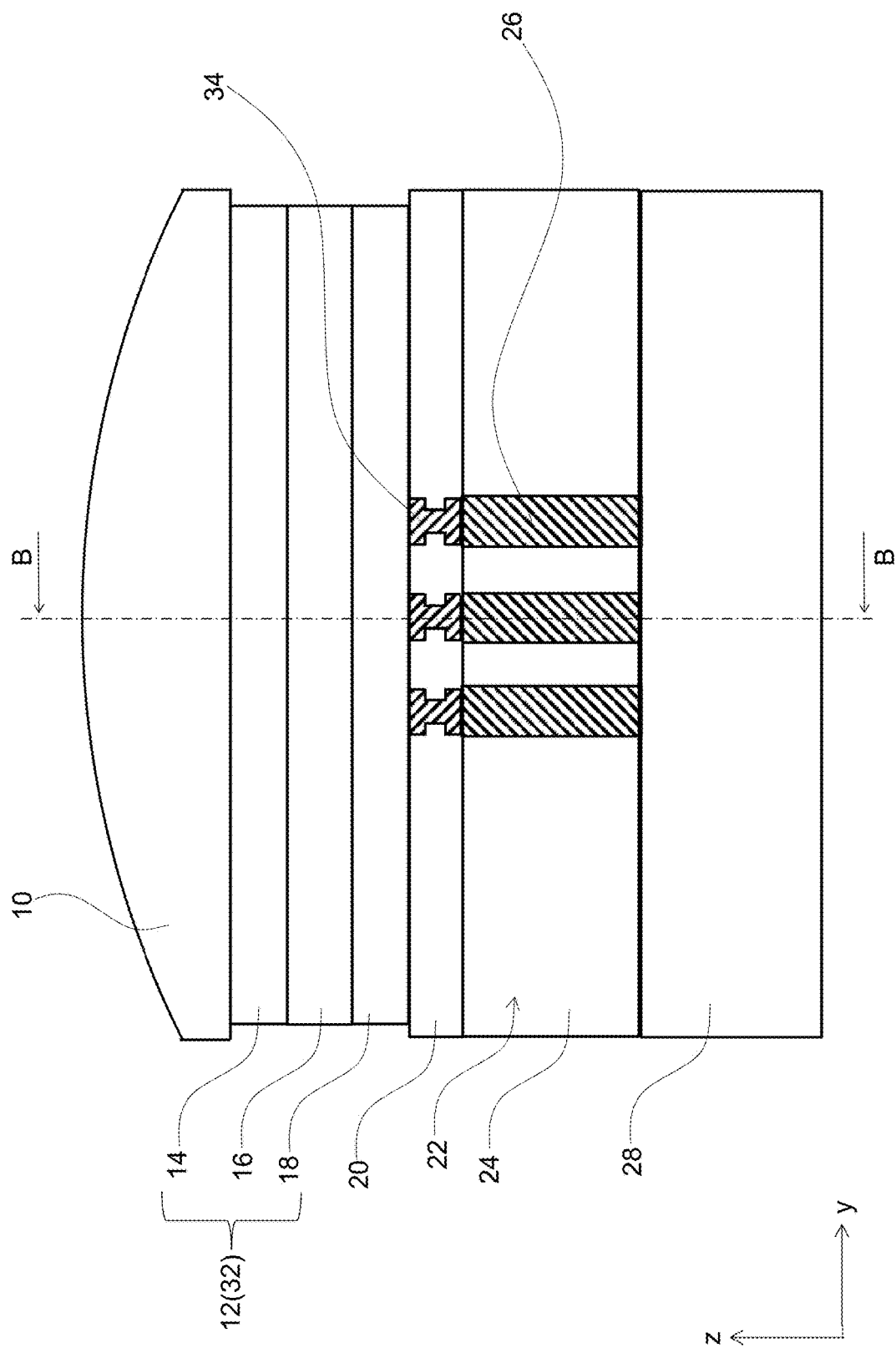
FIG. 5 is a schematic diagram showing a cross section in a long axis direction of an ultrasonic probe.
Figure 6:
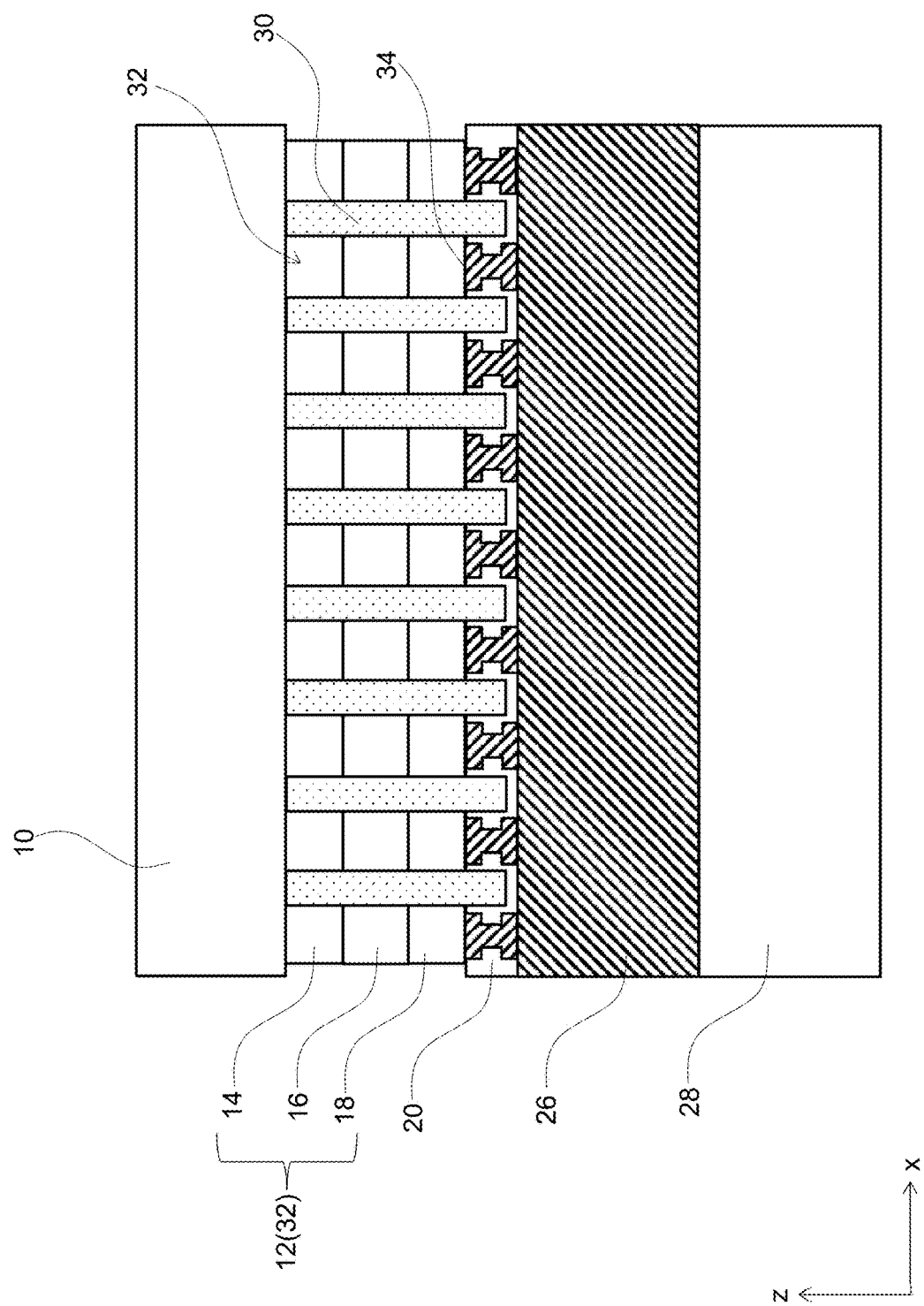
FIG. 6 is a schematic diagram showing a cross section in a short axis direction of an ultrasonic probe.

An ultrasonic probe according to a second embodiment of the present disclosure will now be described. FIG. 5 schematically shows a cross section in the long axis direction of the ultrasonic probe according to the second embodiment of the present disclosure. FIG. 6 shows a cross section in the shot axis direction when the ultrasonic probe is cut along a line BB of FIG. 5. The ultrasonic probe in the second embodiment of the present disclosure differs from the ultrasonic probe of the first embodiment in that the heat dissipation members 26 provided in the backing layer 22 extend in the short axis direction. In addition, a thickness of the wiring layer 20 of the ultrasonic probe of the second embodiment is greater than a thickness of the wiring layer 20 of the ultrasonic probe of the first embodiment.

As shown in FIG. 6, the transduction layer 12 is divided by the cut groove 30 which is parallel to the cross section in the long axis direction, and each of the portions divided by a plurality of cut grooves 30 forms the transducer 32.

The cut groove 30 extends from the front surface of the transduction layer 12 to the rear surface, and further to the wiring layer 20 at the rear side. In the example configuration of FIG. 6, eight cut grooves 30 are formed in equal intervals in the long axis direction, and nine transducers 32 are thereby formed. FIG. 6 shows an ultrasonic probe having nine transducers 32, but the transduction layer 12 may include the transducers 32 in a number of 100 or more and 300 or less.

In the wiring layer 20, a thermal via 34 is provided as a heat conducting structure between the transducer element 32 and the heat dissipation layer 28. The thermal via 34 is provided for each of the plurality of transducers 32, and a plurality of thermal vias 34 are placed along the direction of extension of one heat dissipation member 26. The thermal via 34 is formed in a pillar shape with the front-and-rear direction as an axial direction, and penetrates through the layer-form member forming the wiring layer 20. The pillar shape of the thermal via 34 may be a circular pillar shape or a polygonal pillar shape. The thermal via 34 has a larger size (thickness) at a front end and at a rear end. The thermal via 34 is placed at a position between adjacent cut grooves 30.

In the ultrasonic probe of the present embodiment, an area occupancy percentage of the heat dissipation member 26 at a center region of the cross section in the long axis direction of the backing layer 22 is larger than an area occupancy percentage of the heat dissipation member 26 at an outer side of the center region. The center region is a region which is not positioned at ends of the cross section in the long axis direction, which includes a center of gravity of the cross section in the long axis direction, and which occupies an area of less than or equal to a half of an area of the cross section in the long axis direction. An area of each region at the ends of the cross section in the long axis direction, which is not the center region, is set to, for example, greater than or equal to ⅛ of the area of the cross section in the long axis direction. That is, in the ultrasonic probe of the present embodiment, a volume occupancy percentage of the heat dissipation member 26 in a three-dimensional center region extending in the short axis direction with the center region of the cross section in the long axis direction as a cross section is larger than a volume occupancy percentage of the heat dissipation member 26 at an outer side of the three-dimensional center region.

In the example configuration of FIG. 5, the center region is a region which occupies ⅓ of the cross section of the long axis direction at the center of the cross section in the long axis direction. Specifically, the center region is a region surrounded by a left-side boundary line which extends in the front-and-rear direction at a right side at ⅓ from the vertical side at the left of the figure of the cross section in the long axis direction and a right-side boundary line which extends in the front-and-rear direction at ⅓ from the vertical side at the right of the figure of the cross section in the long axis direction. No heat dissipation member is provided in regions at an outer side of the center region. A center of gravity of the center region coincides with the center of gravity of the cross section in the long axis direction. The heat dissipation member 26 is in thermal contact with the transducer 32 through the thermal via 34 provided in the wiring layer 20. The heat generated by the transducer 32 is transferred to the heat dissipation layer 28 through the thermal via 34 and the heat dissipation member 26 at the rear side of the transducer 32.

In the ultrasonic probe of the present embodiment, the area occupancy percentage of the heat dissipation member 26 at the center region of the cross section in the long axis direction is larger than the area occupancy percentage of the heat dissipation member 26 at the outer side of the center region. With this configuration, the heat dissipation efficiency at the center part from a region near the center of the front surface of the protective layer 10 to the inside can be improved. In the ultrasonic probe, an amount of heat generation is greater at the center part. Thus, according to the present embodiment, the amount of temperature increase of the overall ultrasonic probe can be suppressed. Further, a volume of the heat dissipation member 26 included in the backing layer 22 can be reduced, and the effect of attenuation of the ultrasound in the backing layer 22 can be improved.

In addition, in the ultrasonic probe of the present embodiment, although the cut groove 30 extends from the front surface of the transduction layer 12 to the rear surface and to the wiring layer 20 at the rear side, the cut groove 30 does not extend to the heat dissipation member 26. Moreover, the thermal via 34 is provided at a position between the cut grooves 30 between adjacent transducers 32. With this configuration, in a case where the cut grove 30 is formed after the acoustic matching layer 14, the transducer layer 16, the hard backing layer 18, the wiring layer 20, and the backing layer 22 are layered, contact of a tool for forming the cut groove 30 with the heat dissipation member 26 can be avoided, thereby preventing shortening of the lifetime of the tool. Further, the thermal via 34 is formed in a pillar shape with the front-and-rear direction as an axial direction, and has a larger diameter at the front end and at the rear end. With this configuration, it becomes more difficult for the thermal via 34 to shift in the front-and-rear direction in the wiring layer 20.

Figure 7:
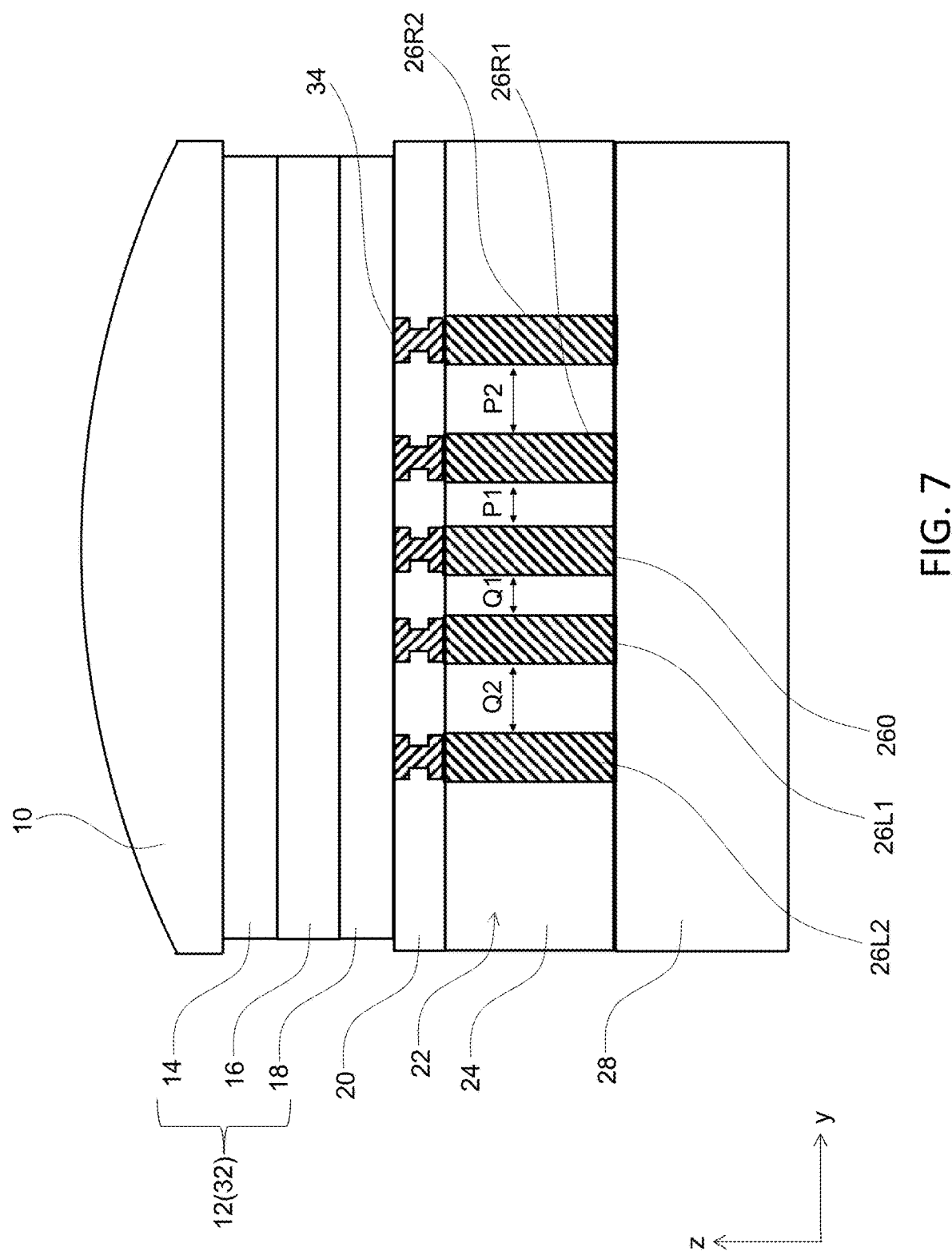
FIG. 7 is a diagram showing a first alternative configuration of an ultrasonic probe according to a second embodiment of the present disclosure.

FIG. 7 shows a first alternative configuration of the ultrasonic probe according to the second embodiment of the present disclosure. In the ultrasonic probe according to this alternative configuration, a placement interval of the heat dissipation members becomes longer from the center toward the outer side in the cross section in the long axis direction of the backing layer 22. For example, when a first heat dissipation member, a second heat dissipation member, and a third heat dissipation member are placed in this order in a direction from the center to the outer side of the cross section in the long axis direction, a distance between the second heat dissipation member and the third heat dissipation member is set longer than a distance between the first heat dissipation member and the second heat dissipation member. The distance between two adjacent heat dissipation members may be defined as a width of a gap formed between the two heat dissipation members. Alternatively, the distance may be defined as a distance between a center line in the front-and-rear direction of one heat dissipation member and a center line in the front-and-rear direction of the other heat dissipation member.

In the example configuration of FIG. 7, a heat dissipation member 260 is placed at a center of the center region. Heat dissipation members 26R1 and 26R2 are placed in this order toward a right direction. In addition, heat dissipation members 26L1 and 26L2 are placed in this order toward a left direction. A distance P2 between the heat dissipation member 26R1 and the heat dissipation member 26R2 is longer than a distance P1 between the heat dissipation member 260 and the heat dissipation member 26R1. Further, a distance Q2 between the heat dissipation member 26L1 and the heat dissipation member 26L2 is longer than a distance Q1 between the heat dissipation member 260 and the heat dissipation member 26L1.

According to such a configuration, an area occupancy percentage of the heat dissipation member 26 at the center region of the cross section in the long axis direction of the backing layer 22 is larger than an area occupancy percentage of the heat dissipation member 26 at the outer side of the center region. With this configuration, the heat dissipation effect at the center part from a region near the center of the front surface of the protective layer 10 to the inside can be improved. In the ultrasonic probe, an amount of heat generation is greater at the center part. Thus, according to the present embodiment, the amount of temperature increase of the overall ultrasonic probe can be suppressed. Further, a volume of the heat dissipation member 26 can be reduced, and the effect of attenuating the ultrasound by the backing layer 22 can be improved.

The regularity of the structure that the placement interval of the heat dissipation members becomes longer from the center toward the outer side may also be employed for the ultrasonic probe of the first embodiment of the present disclosure. In this case, the placement interval of the heat dissipation members becomes longer from the center toward the outer side in the cross section in the short axis direction of the backing layer 22.

Figure 8:
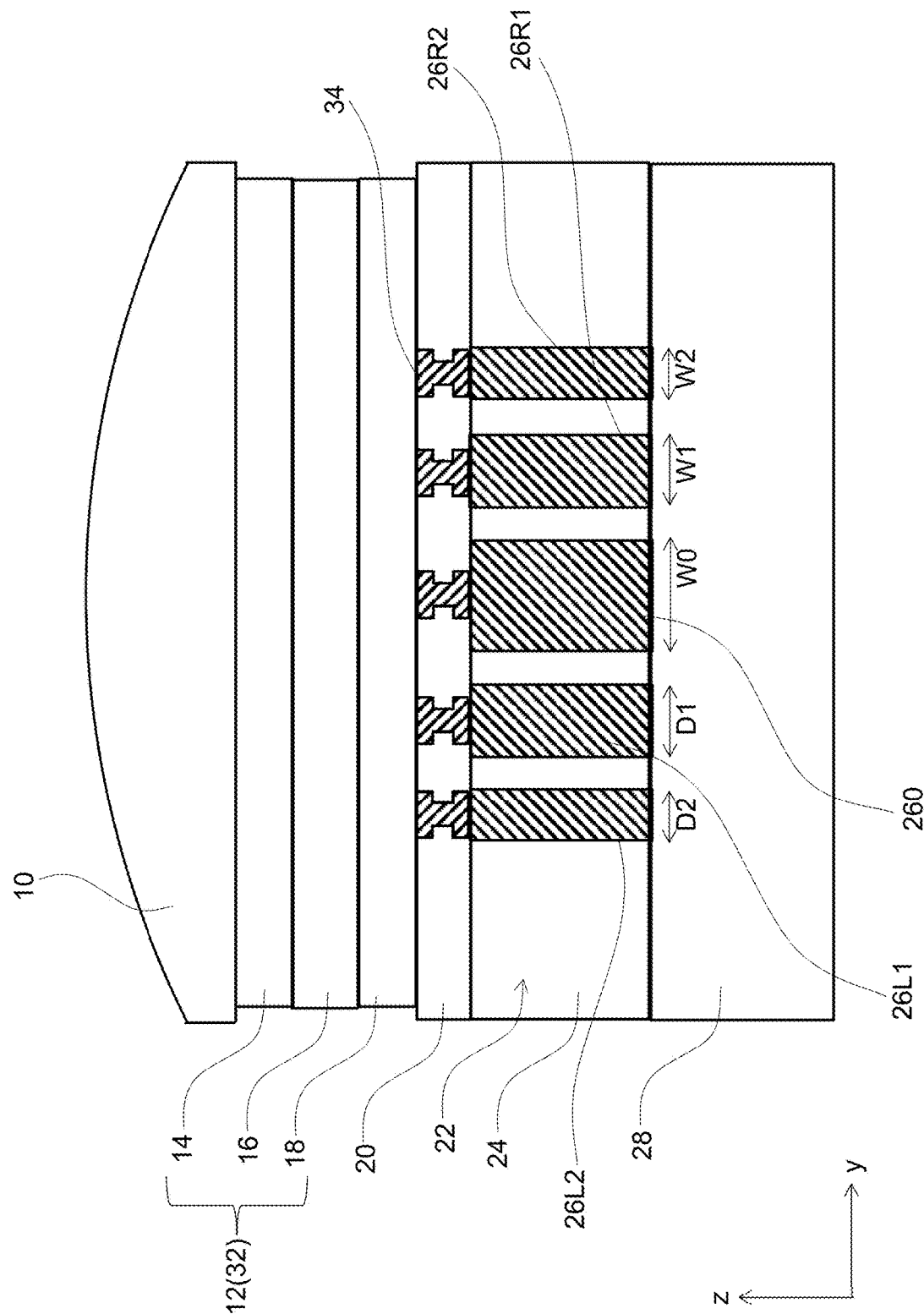
FIG. 8 is a diagram showing a second alternative configuration of an ultrasonic probe according to the second embodiment of the present disclosure.

FIG. 8 shows a second alternative configuration of the ultrasonic probe according to the second embodiment of the present disclosure. In the ultrasonic probe according to this alternative configuration, a width (length in the long axis direction) of the heat dissipation member becomes smaller from the center toward an outer side in the cross section in the long axis direction of the backing layer 22. For example, when a first heat dissipation member, a second heat dissipation member, and a third heat dissipation member are placed in this order from the center toward the outer side of the cross section in the long axis direction, a width of the first heat dissipation member is set larger than a width of the second heat dissipation member. Further, the width of the second heat dissipation member is set larger than a width of the third heat dissipation member.

In the example configuration of FIG. 8, a heat dissipation member 260 is placed at a center of the center region. Heat dissipation members 26R1 and 26R2 are placed in this order toward a right direction. Heat dissipation members 26L1 and 26L2 are placed in this order toward a left direction. A width W2 of the heat dissipation member 26R2 is smaller than a width W1 of the heat dissipation member 26R1, and the width W1 of the heat dissipation member 26R1 is smaller than a width W0 of the heat dissipation member 260. Further, a width D2 of the heat dissipation member 26L2 is smaller than a width D1 of the heat dissipation member 26L1, and the width D1 of the heat dissipation member 26L1 is smaller than the width W0 of the heat dissipation member 260.

The regularity of the structure that the width of the heat dissipation member becomes smaller from the center toward the outer side may also be applied to the ultrasonic probe of the first embodiment of the present disclosure. In this case, the width of the heat dissipation member becomes smaller from the center toward the outer side in the cross section in the short axis direction of the backing layer 22.

Under a condition that an area density of the heat dissipation member in the center region is larger than that in the outer side of the center region, the placement interval of the heat dissipation members, the widths of the heat dissipation members, the number of the heat dissipation members, or the like may be arbitrarily determined.

Figure 9:
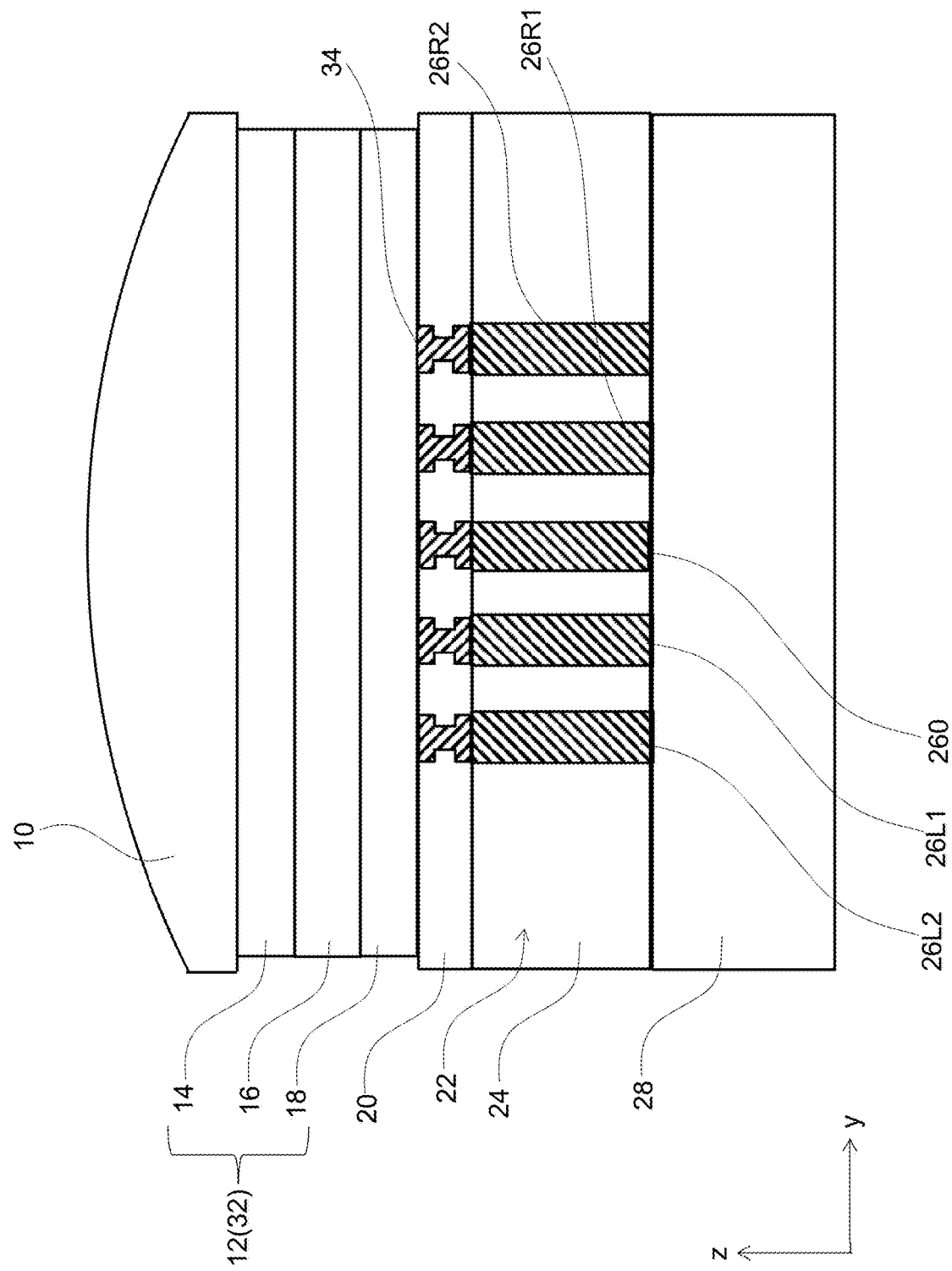
FIG. 9 is a diagram showing a third alternative configuration of an ultrasonic probe according to the second embodiment of the present disclosure.

FIG. 9 shows a third alternative configuration of the ultrasonic probe according to the second embodiment of the present disclosure. In the ultrasonic probe of this alternative configuration, a thermal conductivity of the heat dissipation member becomes higher from an outer side toward the center in the cross section in the long axis direction of the backing layer 22. For example, when a first heat dissipation member, a second heat dissipation member, and a third heat dissipation member are placed in this order from the center in a direction toward the outer side of the cross section in the long axis direction, a thermal conductivity of the first heat dissipation member is set to be higher than a thermal conductivity of the second heat dissipation member. The thermal conductivity of the second heat dissipation member is set to be higher than a thermal conductivity of the third heat dissipation member. The thermal conductivity is a value unique to a material, and indicates ease of conductance of the heat.

In the example configuration of FIG. 9, a heat dissipation member 260 is placed at a center of the center region. Heat dissipation members 26R1 and 26R2 are placed in this order toward a right side. Heat dissipation members 26L1 and 26L2 are placed in this order toward a left side. A thermal conductivity of the heat dissipation member 26R1 is higher than a thermal conductivity of the heat dissipation member 26R2, and a thermal conductivity of the heat dissipation member 260 is higher than the thermal conductivity of the heat dissipation member 26R1. Further, a thermal conductivity of the heat dissipation member 26L1 is higher than a thermal conductivity of the heat dissipation member 26L2, and the thermal conductivity of the heat dissipation member 260 is higher than the thermal conductivity of the heat dissipation member 26L1.

The heat dissipation member 260 is formed from, for example, aluminum nitride. The heat dissipation members 26R1 and 26L1 are formed from, for example, silicon nitride. The heat dissipation members 26R2 and 26L2 are formed from, for example, aluminum oxide. Silicon nitride has a higher thermal conductivity than aluminum oxide, and aluminum nitride has a higher thermal conductivity than silicon nitride.

The regularity of the structure that the thermal conductivity of the heat dissipation members becomes higher from the outer side toward the center may also be applied to the ultrasonic probe of the first embodiment of the present disclosure. In this case, the thermal conductivity of the heat dissipation member becomes higher from the outer side toward the center in the cross section in the short axis direction of the backing layer 22.

The invention claimed is:

1. An ultrasonic probe comprising:
   a transduction layer in which a plurality of transducers are placed;
   a backing layer provided at a rear side of the transduction layer; and
   a plurality of heat dissipation members which are provided in the backing layer, wherein the heat dissipation members extend in a line form in the backing layer in a long axis of the ultrasonic probe and are placed with an aligned direction of extension,
   wherein an area occupancy percentage of the heat dissipation members relative to the backing layer at a center region of the backing layer in a cross section along a short axis intersecting the long axis is larger than the area occupancy percentage of the heat dissipation members relative to the backing layer at a region at an outer side of the center region.

2. The ultrasonic probe according to claim 1, wherein the center region is a region which is not positioned at ends of the cross section, which includes a center of gravity of the cross section, and which occupies an area less than or equal to a half of an area of the cross section.

3. The ultrasonic probe according to claim 1, wherein each of the transducers extends in the long axis direction, and is placed in an arrangement along the short axis direction intersecting the long axis direction, and
   the heat dissipation members extend in the long axis direction, and are placed a positions between cut grooves extending from gaps between two adjacent transducers to the backing layer.

4. The ultrasonic probe according to claim 1, further comprising:
   a wiring layer provided between the transduction layer and the backing layer, wherein
   each of the transducers extend in the long axis direction, and is placed in an arrangement along the short axis direction intersecting the long axis direction, and
   the heat dissipation members extend in the short axis direction, and the wiring layer has a heat conducting structure.

5. The ultrasonic probe according to claim 4, wherein the heat conducting structure includes thermal vias provided between the transducers and the heat dissipation members.

6. The ultrasonic probe according to claim 5, wherein the thermal vias are provided at positions between cut grooves extending from gaps between two adjacent transducers to the wiring layer.

7. The ultrasonic probe according to claim 4, further comprising:
   a cut groove extending from a gap between two adjacent transducers to the wiring layer.

8. The ultrasonic probe according to claim 1, wherein a placement interval of the plurality of heat dissipation members becomes wider from a center of the center region toward an outer side.

9. The ultrasonic probe according to claim 1, wherein a width in a direction of placement of the plurality of heat dissipation members becomes greater from an outer side of the center region of the backing layer toward a center of the backing layer.

10. The ultrasonic probe according to claim 1, wherein thermal conductivities of materials forming the plurality of heat dissipation members become higher from an outer side of the center region of the backing layer toward a center of the backing layer.

* * * * *